United States Patent
Brezeanu et al.

(10) Patent No.: US 9,291,594 B2
(45) Date of Patent: Mar. 22, 2016

(54) CO2 SENSOR BASED ON A DIAMOND FIELD EFFECT TRANSISTOR

(71) Applicant: HONEYWELL INTERNATIONAL INC., Morristown, NJ (US)

(72) Inventors: Mihai Brezeanu, Bucharest (RO); Bogdan Catalin Serban, Bucharest (RO); Octavian Buiu, Bucharest (RO); Viorel Georgel Dumitru, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/573,221

(22) Filed: Dec. 17, 2014

(65) Prior Publication Data

US 2015/0177184 A1      Jun. 25, 2015

(30) Foreign Application Priority Data

Dec. 24, 2013    (EP) .................................... 13199569

(51) Int. Cl.
  *H01L 29/15*   (2006.01)
  *G01N 27/414*  (2006.01)
  *G01N 33/00*   (2006.01)

(52) U.S. Cl.
  CPC .......... *G01N 27/4141* (2013.01); *G01N 33/004* (2013.01)

(58) Field of Classification Search
  CPC ....................... G01N 27/4141; G01N 33/004
  USPC ................................................. 257/77, 414
  See application file for complete search history.

(56) References Cited

U.S. PATENT DOCUMENTS

2005/0129573 A1    6/2005  Gabriel et al.
2008/0264147 A1*  10/2008  Serban et al. ............... 73/24.06
2011/0146382 A1    6/2011  Fleischer et al.

FOREIGN PATENT DOCUMENTS

DE      102009040052 A1     3/2011

OTHER PUBLICATIONS

"European Application Serial No. 13199569.8, Examination Notification Art. 94(3) mailed Jun. 13, 2014", 5 pgs.
"European Application Serial No. 13199569.8, Extended European Search Report mailed May 19, 2014", 4 pgs.
Ahmed, Razal, et al., "Nanodiamond-gated diamond field-effect transistor for chemical sensing using hydrogen-Induced transfer doping for channel formation", Applied Physics Letters, American vol. 97, No. 20, (Nov. 17, 2010), 203503-203503.
Anderson, T., et al., "Advances in Hydrogen, Carbon Dioxide, and Hydrocarbon Gas Sensor Technology Using GaN and ZnO-Based Devices", Sensors, 9, (2009), 4669-4694.

(Continued)

*Primary Examiner* — Tu-Tu Ho
(74) *Attorney, Agent, or Firm* — Schwegman Lundberg & Woessner, P.A.

(57) ABSTRACT

The present disclosure relates to a carbon dioxide sensor able to function in harsh environment, conditions. The carbon dioxide sensor can include a gate-less field effect transistor including a synthetic, quasi-intrinsic, hydrogen-passivated, single-crystal diamond layer exhibiting a 2-dimension hole gas effect, and a sensing layer comprising both a polymer and a hygroscopic material deposited onto a surface of the gate-less field effect transistor.

13 Claims, 1 Drawing Sheet

(56) References Cited

OTHER PUBLICATIONS

Garrido, Jose, et al., "pH sensors based on hydrogenated diamond surfaces", Applied Physics Letter, American Institute of Physics vol. 86, No. 7, (Feb. 9, 2005), 73504-073504.

Helwig, A, et al., "Gas Sensing Interactions at Hydrogenated Diamond Surfaces", IEEE Sensors Journal, IEEE Service Center New York vol. 7, No. 9, (Sep. 1, 2007), 1349-1353.

Helwig, A., et al., "Gas sensing properties of hydrogen-terminated diamond", Sensors and Actuators B, 133, (2008), 156-165.

Hokazono, A, et al., "Surface p-channel metal-oxide-semiconductor field effect transistors fabricated on hydrogen terminated (001) surfaces of diamond", Solid State Electronics, Elsvier Science Publisher, Barking vol. 43, No. 8, (Aug. 1, 1999), 1465-1471.

Kubovic, M., et al., "Structural and electrical properties of H-terminated diamond field-effect transistor", Diamond & Related Materials, 18, (2009), 796-799.

Landstrass, M. I, et al., "Hydrogen passivation of electrically active defects in diamond", Appl. Phys. Lett., 55, (1989), 1391-1393.

* cited by examiner

CO2 SENSOR BASED ON A DIAMOND FIELD EFFECT TRANSISTOR

BACKGROUND

Chemical sensors are widely used in industrial environments for process control, environmental control, and other applications. A chemical sensor is a device which monitors the concentration of a given chemical species in a liquid or a gas. Chemical sensor are often required to be highly sensitive, in order to detect small concentrations of the chemical. They are also often required to withstand harsh chemical environments and/or high temperatures which may be present in process control, environmental control or other applications. For example, carbon dioxide sensors have been used in normal ambient, as well as in harsh environment conditions (e.g., high radiation levels, high corrosion rates, high humidity levels, and high temperatures). Chemical sensors employing wide band gap semiconducting materials, such as silicon carbide, gallium nitride, synthetic diamond, are prone to withstand harsh environment conditions.

SUMMARY

The examples of the present disclosure provide carbon dioxide ($CO_2$) sensors based on a diamond field effect transistor, for example, a gate-less field effect transistor.

Example 1 includes subject matter directed toward a carbon dioxide sensor. The carbon dioxide sensor can include a gate-less field effect transistor including a synthetic, quasi-intrinsic, hydrogen-passivated, single-crystal diamond layer exhibiting a 2-dimension hole gas effect, and a sensing layer including a polymer and a hygroscopic material deposited onto a surface of the gate-less field effect transistor.

In Example 2, the subject matter of Example 1 can be optionally configured such that the gate-less field effect transistor includes an ohmic drain contact and an ohmic source contact.

In Example 3, the subject matter of Examples 1 or 2 can be optionally configured such that two highly-doped p-type regions are implanted within the synthetic, quasi-intrinsic, hydrogen-passivated, single-crystal diamond layer, wherein a first highly-doped p-type region is positioned below the ohmic source contact and a second highly-doped p-type region is positioned below the ohmic drain contact.

In Example 4, the subject matter of Examples 1-3 can be optionally configured to include one of a single-crystal diamond structure and a poly-crystalline diamond structure.

In Example 5, the subject matter of Examples 1-4 can be optionally configured such that the one of the single-crystal diamond substrate and the poly-crystalline diamond substrate is connected to an ohmic substrate contact.

In Example 6, the subject matter of Examples 1-5 can be optionally configured such that the synthetic, quasi-intrinsic, hydrogen-passivated, single-crystal diamond layer is positioned on a top surface of the one of the single-crystal diamond substrate and the poly-crystalline diamond substrate.

In Example 7, the subject matter of Examples 1-6 can be optionally configured to include a 2-dimension hole gas channel within the synthetic, quasi-intrinsic, hydrogen-passivated, single-crystal diamond layer.

In Example 8, the subject matter of Examples 1-7 can be optionally configured such that the sensing layer is positioned between an ohmic drain contact and an ohmic source contact, and adjacent to the 2-dimension hole gas channel.

In Example 9, the subject matter of Examples 1-8 can be optionally configured such that the polymer is chosen from at least one of polyallylamine, N-substituted polyallylamine, polydiallylamine, polyvinylamine, N-substituted polyvinylamine, polyethylenimine, and a nanocomposite matrix.

In Example 10, the subject matter of Examples 1-9 can be optionally configured such that the nanocomposite matrix includes: at least one of polyallylamine, N-substituted polyallylamine, polydiallylamine, polyvinylamine, N-substituted polyvinylamine, and polyethylenimine; and aminomethil carbon nanotubes.

In Example 11, the subject matter of Examples 1-10 can be optionally configured such that the hygroscopic material is chosen from at least one of cyclodextrines, xylitol, maltitol, and polydextrose.

Example 12 includes subject matter directed toward a method. The method can include providing or obtaining a gate-less field effect transistor including a synthetic, quasi-intrinsic, hydrogen-passivated, single-crystal diamond layer exhibiting a 2-dimension hole gas effect, providing or obtaining a sensing layer including a polymer and a hygroscopic material, and depositing the sensing layer onto a surface of the gate-less field effect transistor.

In Example 13, the subject matter of Examples 1-12 can be optionally configured such that providing or obtaining the gate-less field effect transistor includes growing a synthetic, quasi-intrinsic, hydrogen-passivated, single-crystal diamond layer on top of one of a single-crystal diamond structure and a poly-crystalline diamond substrate.

In Example 14, the subject matter of Examples 1-13 can be optionally configured such that the polymer is chosen from at least one of polyallylamine, N-substituted polyallylamine, polydiallylamine, polyvinylamine, N-substituted polyvinylamine, polyethylenimine, and a nanocomposite matrix. The nanocomposite matrix includes at least one of polyallylamine, N-substituted polyallylamine, polydiallylamine, polyvinylamine, N-substituted polyvinylamine, and polyethylenimine; and aminomethil carbon nanotubes.

In Example 15, the subject matter of Examples 1-14 can be optionally configured such that the hygroscopic material is chosen from one of cyclodextrines, xylitol, maltitol, and polydextrose.

DETAILED DESCRIPTION OF THE DRAWINGS

The embodiments of the present invention will be described, by way of example only, by reference to the FIGS. 1 and 2 of the accompanying drawings in which.

DETAILED DESCRIPTION

Figure 1:
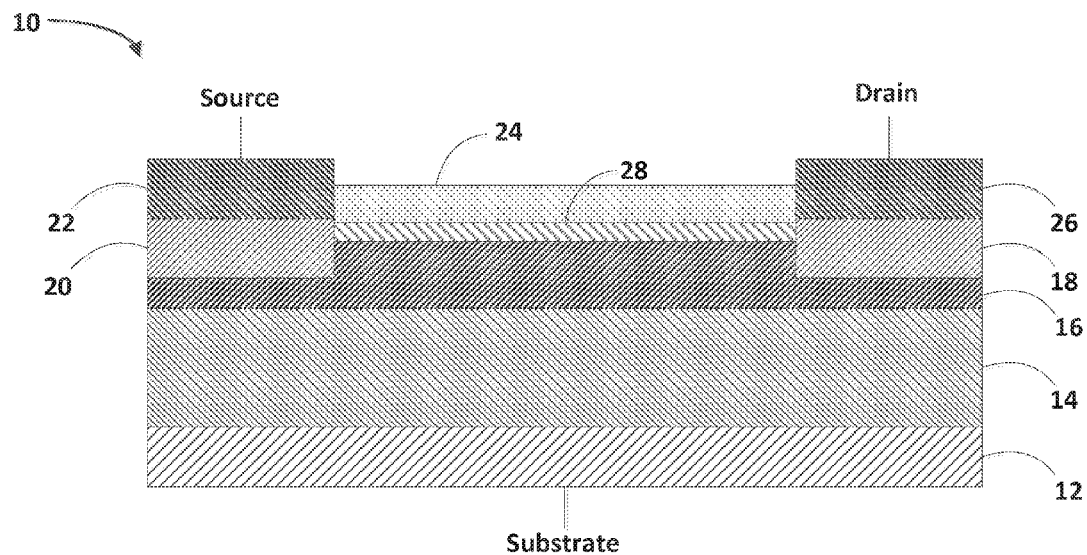
FIG. 1 shows a cross-sectional view of a $CO_2$ sensor, in accordance with one example.

Examples of the present disclosure relate to a carbon dioxide sensor and method of making the carbon dioxide sensor. Carbon dioxide sensors can be used in applications such as combustions and emission monitoring in domestic and industrial boilers, in car and plane engines, the food industry, carbon storage and sequestration, oil and gas storage, and transportation. These applications generally require carbon dioxide sensors with increased sensitivity levels, lower response time, reduced dimensions, and longer lifetime. The carbon dioxide sensors of the present disclosure can have a high $CO_2$ sensitivity and limited cross-sensitivity. The carbon dioxide sensors are built on synthetic diamond, the hardest known material, and are able to be used in harsh conditions (e.g., temperatures up to 150 degrees Celsius, relative humidity levels up to 100%, high radiation levels, high corrosion rates).

Previous approaches for $CO_2$ sensors included semiconductors such as silicon or silicon carbide. However, the previous $CO_2$ sensors do not match the sensitivity level, response time, dimensions, and lifetime required for operation in harsh conditions.

In some examples, the carbon dioxide sensor can include a gate-less field effect transistor including a synthetic, quasi-intrinsic, single-crystal diamond layer exhibiting a 2-dimension hole gas effect. The carbon dioxide sensor can include a sensing layer. The sensing layer can include both a polymer and a hygroscopic material and is deposited onto a surface of the gate-less field effect transistor. The gate-less field effect transistor does not include a gate.

In some examples, the carbon dioxide sensor can include a synthetic diamond substrate, which can be either single-crystal or poly-crystalline, and an ohmic contact to the substrate. In an example, a synthetic, quasi-intrinsic, single-crystal diamond layer can be grown and hydrogen-passivated on the synthetic diamond substrate forming a synthetic, quasi-intrinsic, hydrogen-passivated, single-crystal, diamond layer (also referred to herein as a "quasi-intrinsic diamond layer"). The quasi-intrinsic diamond layer can be grown by chemical vapor deposition (CVD). A 2-dimension (2D) conductive channel can form along the surface of the quasi-intrinsic diamond layer. The 2D conductive channel can consist of holes (2D hole gas (HG) effect), phenomen which refers to the presence of a gas of holes, free to move in two dimensions only. This effect naturally occurs at the surface of the synthetic, quasi-intrinsic, hydrogen-passivated, single-crystal diamond layer. In an example, the sensing layer can be adjacent to the 2D conductive channel. That is, the sensing layer is deposited onto a surface of the gate-less field effect transistor that is above the 2D conductive channel.

In an example, the carbon dioxide sensor can further include an ohmic substrate contact, an ohmic source contact, and an ohmic drain contact. In an example, two highly doped p-type regions can be created within the quasi-intrinsic diamond layer. In an example, the two highly doped p-type regions can be positioned right below the ohmic source contact and the ohmic drain contact, respectively. For example, the p-type regions can be created by ion implementation (e.g., with Boron atoms) and a doping concentration, for example, can be about $10^{20}$ cm$^{-3}$.

In an example, the sensing layer includes both a polymer and a hygroscopic material and can be deposited onto the surface of the quasi-intrinsic diamond layer and between the two ohmic contacts (e.g., the ohmic source contact and the ohmic drain contact). The sensing layer can be deposited onto the surface via spin coating, spray coating, dip coating, or direct printing.

The ohmic drain contact and the ohmic source contact can collect the current flowing through the 2D conductive channel. The carbon dioxide sensor is normally "on", which means that, even at zero Volts (V) gate bias, a current will flow from the source to the drain if there is a potential difference between the ohmic source contact and the ohmic drain contact. The present disclosure maximizes the area exposed to the carbon dioxide by not utilizing a gate. When changes occur in the carbon dioxide concentration, the potential at the surface of the gate-less field effect transistor (e.g., below and along the sensing layer) changes, thus leading to a variation in the 2D conductive channel carrier concentration, which results into a change of the drain-source current.

As discussed herein, the sensing layer can include both a polymer and a hygroscopic material. The sensing layer can be selected based on the Hard Soft Acid Base (HSAB) theory. That is, hard Lewis bases prefer to bond to hard Lewis acids, and soft Lewis bases prefer to bond to soft Lewis acids. Carbon dioxide is considered to be an example of a hard acid, according to the HSAB theory.

In an example, the polymer within the sensing layer can be chosen from at least one of polyallylamine (PAA), N-substituted polyallylamine, polyvinylamine, N-substituted polyvinylamine, polyethylenimine (PEI), and a nanocomposite matrix. The nanocomposite matrix can include a mixture of aminomethil carbon nanotubes (CNTs) and at least one of polyallylamine, N-substituted polyallylamine, polydiallylamine, polyvinylamine, N-substituted polyvinylamine, and polyethylenimine. In an example, the aminomethil carbon nanotubes can be single wall, double-wall, or multiple-wall carbon nanotubes. The polymers disclosed are considered hard bases, according to the HSAB theory, and thus, have strong interaction with carbon dioxide molecules, which are hard acids.

In an example, at least one hygroscopic material is mixed with the polymer. In an example, the hydroscopic material can be chosen from cyclodextrines ($\alpha$, $\beta$, $\gamma$, or mixtures thereof), xylitol, maltitol, polydextrose, and mixtures thereof. The hygroscopic material, in some embodiments, is sufficiently hygroscopic so as to provide sufficient moisture (e.g., maintain a sufficient level of humidity) in order to trigger the ionization of carbon dioxide.

FIG. 1 shows a cross-sectional view of a $CO_2$ sensor 10 (referred to herein as "sensor 10"), in accordance with one example. The sensor 10 can include an ohmic substrate contact 12, a diamond substrate 14 (e.g., either a single-crystal or poly-crystalline diamond substrate), a synthetic, quasi-intrinsic, hydrogen-passivated single-crystal diamond layer 16 (also referred to herein as "quasi-intrinsic diamond layer 16"), and a 2-dimensional hole gas channel 28.

The ohmic substrate contact 12 can include metal stacks such as, but not limited to, titanium-aluminum, titanium-gold, titanium-platinum, and titanium-nickel. In an example, the sensor 10 can include omhic contacts such as a ohmic source contact 22 and a ohmic drain contact 26. The ohmic source contact 22 and the ohmic drain contact 26 can include metal stacks such as, but not limited to, titanium-aluminum, titanium-gold, titanium-platinum, and titanium-nickel. As shown in FIG. 1, the 2-dimensional hole gas channel 28 can form along the surface of the quasi-intrinsic diamond layer 16. The sensing layer 24 can be deposited on the surface of the quasi-intrinsic diamond layer 16 that is adjacent to the 2-dimensional hole gas channel 28.

In an example, the sensor 10 can include two highly doped p-type regions implanted within the quasi-intrinsic diamond layer 16. For example, sensor 10 can include a first highly doped p-type region 20 and a second highly doped p-type region 18. The first highly-doped p-type region 20 can be positioned below the ohmic source contact 22 and the second highly-doped p-type region 18 can be positioned below the ohmic drain contact 26. In an example, the highly doped p-type regions 20 and 18 can be created by ion implementation (e.g., with Boron atoms) and have a doping concentration of about $10^{20}$ cm$^{-3}$. In an example, the highly doped p-type regions 20 and 18 can have a doping concentration between about $10^{19}$ cm$^{-3}$ to about $5 \times 10^{20}$ cm$^{-3}$, for example, about $5 \times 10^{19}$ cm$^{-3}$ to about $2 \times 10^{20}$ cm$^{-3}$, such as $10^{20}$ cm$^{-3}$.

The sensing layer 24 of the sensor 10 can include both the polymer and the hygroscopic material. In an example, the polymer can be chosen from at least one of polyallylamine, N-substituted polyallylamine, polydiallylamine, polyvinylamine, N-substituted polyvinylamine, polyethylenimine, and a nanocomposite matrix. The nanocomposite matrix can include aminomethil carbon nanotubes and at least one of polyallylamine, N-substituted polyallylamine, polydiallylamine, polyvinylamine, N-substituted polyvinylamine, and polyethylenimine. In an example, the hygroscopic material can be chosen from at least one of cyclodextrines (either α, β, γ, or mixtures thereof), xylitol, maltitol, and polydextrose.

In an example, the sensing layer 24 includes about 60 weight percent to about 80 weight percent of the polymer, for example, 65 weight percent to about 75 weight percent, such as about 70 weight percent. The weight percent based on a total weight of the sensing layer 24. In an example, the sensing layer 24 includes about 40 weight percent to about 20 weight percent of the hygroscopic material, for example, 35 weight percent to about 25 weight percent, such as about 30 weight percent. The weight percent based on a total weight of the sensing layer 24.

In an example, the sensing layer 24 includes a mixture of polyallylamine and cyclodexytrines (either α, β, γ, or mixtures thereof).

In an example, the sensing layer 24 includes a mixture of a nanocomposite matrix including polyallylamine and aminomethil carbon nanotubes and cyclodextrines (either α, β, γ, or mixtures thereof).

In an example, the sensing layer 24 includes a mixture of N-substituted polyallylamine and cyclodextrines with alkyl groups. Examples of alkyl groups include, but are not limited to, methyl, ethyl, n-propyl, isopropyl, n-butyl, s-butyl, t-butyl, isobutyl, n-pentyl, tert-pentil, n-hexyl, and 2-methylplentyl.

In an example, the sensing layer 24 includes a mixture of a nanocomposite including N-substituted polyallylamine and aminocarbon nanotubes and cyclodextrines (either α, β, γ, or mixtures thereof).

In an example, the sensing layer 24 includes a mixture of a polyvinylamine and cyclodextrines (either α, β, γ, or mixtures thereof).

In an example, the sensing layer 24 includes a mixture of a nanocomposite matrix including N-substituted polyvinylamine and aminomethil carbon nanotubes and cyclodextrines (either α, β, γ, or mixtures thereof).

In an example, the sensing layer 24 includes a mixture of N-substituted polyvinylamine with alkyl groups and cyclodextrines (either α, β, γ, or mixtures thereof).

In an example, the sensing layer 24 includes a mixture of a nanocomposite matrix including N-substituted polyninylamine with alkyl groups and aminomethil carbon nanotubes and cyclodextrines (either α, β, γ, or mixtures thereof).

In an example, the sensing layer 24 includes a mixture of a polydiallylamine and cyclodextrines (either γ, β, γ, or mixtures thereof).

In an example, the sensing layer 24 includes a mixture of a nanocomposite matrix including polyallylamine and aminomethil carbon nanotubes and cyclodextrines (either α, β, γ, or mixtures thereof).

In an example, the sensing layer 24 includes a mixture of polyallylamine, polyvinylamine, and cyclodextrines (either α, β, γ, or mixtures thereof).

In an example, the sensing layer 24 includes a mixture of polyallylamine, N-substituted polyallylamine, and cyclodextrines (either α, β, γ, or mixtures thereof).

In an example, the sensing layer 24 includes a mixture of polyethyleneimine and cyclodextrines (either α, β, γ, or mixtures thereof).

In an example, the sensing layer 24 includes a mixture of a nanocomposite matrix including polyethyleneimine and aminomethil carbon nanotubes and cyclodextrines.

Figure 2:
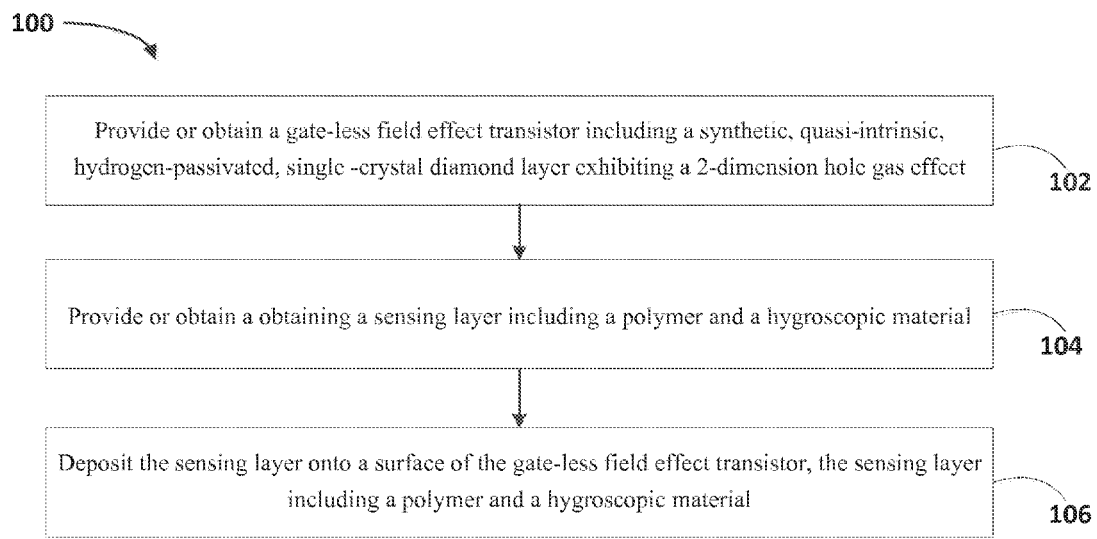
FIG. 2 shows a method of forming a $CO_2$ sensor, in accordance with one example.

FIG. 2 shows a method 100 of forming a $CO_2$ sensor, in accordance with one example. The method 100 of forming a carbon dioxide sensor can include at step 102 provide or obtain a gate-less field effect transistor based on a synthetic, quasi-intrinsic, hydrogen-passivated, single-crystal diamond layer exhibiting a 2-dimension hole gas effect, at step 104 provide or obtain a sensing layer including a polymer and a hygroscopic material, and at step 106 deposit the sensing layer onto a surface of the gate-less field effect transistor, the sensing layer including a polymer and a hygroscopic material.

Providing or obtaining the gate-less field effect transistor can include providing or obtaining an ohmic substrate contact (e.g., ohmic substrate contact 12), a synthetic, either single-crystal or poly-crystalline diamond substrate 14, a quasi-intrinsic diamond layer 16, and a 2-dimensional hole gas channel 28. Method 100 can include growing the quasi-intrinsic diamond layer on top of the diamond substrate (e.g., either a single-crystal or poly-crystalline diamond substrate). Growing the quasi-intrinsic diamond layer on top of the diamond substrate can be done via chemical vapor deposition (CVD).

Providing or obtaining the sensing layer at step 104 can include combining a polymer with a hygroscopic material. For example, the polymer can include at least one of polyallylamine, N-substituted polyallylamine, polydiallylamine, polyvinylamine, N-substituted polyvinylamine, polyethylenimine, and a nanocomposite matrix. The nanocomposite matrix can include at least one of polyallylamine, N-substituted polyallylamine, polydiallylamine, polyvinylamine, N-substituted polyvinylamine, and polyethylenimine, and aminomethil carbon nanotubes. In an example, the hygroscopic material is chosen from one of cyclodextrines, xylitol, maltitol, and polydextrose.

Depositing the sensing layer onto the surface of the gate-less field effect transistor can include spine coating, spray coating, dip coating, or direct printing the sensing layer onto the surface of the gate-less field effect transistor. In an example, after depositing the sensing layer, the sensor can be dried, for example, for 1 hour at, for example, 500 degrees Celsius.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "varus/valgus angle" is used to refer to a varus angle only, a valgus angle only, or both a varus angle and a valgus angle.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

All publications, including non-patent literature (e.g., scientific journal articles), patent application publications, and patents mentioned in this specification are incorporated by reference as if each were specifically and individually indicated to be incorporated by reference.

The Abstract is provided to allow the reader to quickly ascertain the nature of the technical disclosure. It is submitted with the understanding that it will not be used to interpret or limit the scope or meaning of the claims.

What is claimed is:

1. A carbon dioxide sensor, comprising:
   a gate-less field effect transistor including a synthetic, quasi-intrinsic, hydrogen-passivated, single-crystal diamond layer exhibiting a 2-dimension hole gas effect; and
   a sensing layer including a polymer and a hygroscopic material deposited onto a surface of the gate-less field effect transistor, wherein two highly-doped p-type regions are implanted within the synthetic, quasi-intrinsic, hydrogen-passivated, single crystal diamond layer, a first highly-doped p-type region positioned below an ohmic source contact and a second highly-doped p-type region positioned below an ohmic drain contact.

2. The carbon dioxide sensor of claim 1, wherein the gate-less field effect transistor includes an ohmic drain contact and an ohmic source contact.

3. The carbon dioxide sensor of claim 1, comprising one of a single-crystal diamond structure and a poly-crystalline diamond structure.

4. The carbon dioxide sensor of claim 3, wherein the one of the single-crystal diamond substrate and the poly-crystalline diamond substrate is connected to an ohmic substrate contact.

5. The carbon dioxide sensor of claim 1, wherein the synthetic, quasi-intrinsic, hydrogen-passivated, single-crystal diamond layer is positioned on a top surface of the one of the single-crystal diamond substrate and the poly-crystalline diamond substrate.

6. The carbon dioxide sensor of claim 1, comprising a 2-dimension hole gas channel within the synthetic, quasi-intrinsic, hydrogen-passivated, single-crystal diamond layer.

7. The carbon dioxide sensor of claim 6, wherein the sensing layer is positioned between an ohmic drain contact and an ohmic source contact, and adjacent to the 2-dimension hole gas channel.

8. The carbon dioxide sensor of claim 1, wherein the polymer is chosen from at least one of polyallylamine, N-substituted polyallylamine, polydiallylamine, polyvinylamine, N-substituted polyvinylamine, polyethylenimine, and a nanocomposite matrix.

9. The carbon dioxide sensor of claim 8, wherein the nanocomposite matrix includes:
   at least one of polyallylamine, N-substituted polyallylamine, polydiallylamine, polyvinylamine, N-substituted polyvinylamine, and polyethylenimine; and aminomethil carbon nanotubes.

10. The carbon dioxide sensor of claim 1, wherein the hygroscopic material is chosen from at least one of cyclodextrines, xylitol, maltitol, and polydextrose.

11. A method of forming a carbon dioxide sensor, comprising:
   providing or obtaining a gate-less field effect transistor including a synthetic, quasi-intrinsic, hydrogen-passivated, single-crystal diamond layer exhibiting a 2-dimension hole gas effect;
   providing or obtaining a sensing layer including a polymer and a hygroscopic material, wherein the hygroscopic material is chosen from one of cyclodextrines, xylitol, maltitol, and polydextrose; and
   depositing the sensing layer onto a surface of the gate-less field effect transistor.

12. The method of claim 11, wherein providing or obtaining the gate-less field effect transistor includes growing a synthetic, quasi-intrinsic, hydrogen-passivated, single-crystal diamond layer on top of one of a single-crystal diamond structure and a poly-crystalline diamond substrate.

13. The method of claim 11, wherein the polymer is chosen from at least one of polyallylamine, N-substituted polyallylamine, polydiallylamine, polyvinylamine, N-substituted polyvinylamine, polyethylenimine, and a nanocomposite matrix, the nanocomposite matrix includes:
   at least one of polyallylamine, N-substituted polyallylamine, polydiallylamine, polyvinylamine, N-substituted polyvinylamine, and polyethylenimine; and aminomethil carbon nanotubes.

* * * * *